United States Patent [19]

Kitamura et al.

[11] 4,419,888

[45] Dec. 13, 1983

[54] HUMIDITY MEASURING METHOD

[75] Inventors: Kenzo Kitamura, Tokyo; Tetsuo Miura, Omiya; Satoshi Ookubo, Hasuda; Hideyuki Nagata, Urawa, all of Japan

[73] Assignee: Kabushikikaisha Shibaura Denshi Seisakusho, Japan

[21] Appl. No.: 148,465

[22] Filed: May 9, 1980

[30] Foreign Application Priority Data

Jun. 14, 1979 [JP] Japan .................................. 54-74858
Jun. 14, 1979 [JP] Japan ............................. 54-81092[U]
Jun. 14, 1979 [JP] Japan ............................. 54-81093[U]

[51] Int. Cl.³ ...................... G01W 1/02; G01W 25/18
[52] U.S. Cl. .................................. 73/336.5; 73/27 R
[58] Field of Search ............................ 73/336.5, 27 R

[56] References Cited

U.S. PATENT DOCUMENTS

| | | | |
|---|---|---|---|
| 1,701,181 | 2/1929 | Gross | 73/27 R |
| 1,855,774 | 4/1932 | Schneider | 73/336.5 |
| 2,077,538 | 4/1937 | Wait | 73/27 R |
| 2,116,239 | 5/1938 | Hebler | 73/27 R |
| 2,205,306 | 6/1940 | Olshersky | 73/27 R |
| 3,184,953 | 5/1965 | Petrocelli | 73/27 R |
| 3,187,558 | 6/1965 | Koncen et al. | 73/27 R |

OTHER PUBLICATIONS

Daynes, H. A., *Gas Analysis by Measurement of Thermal Conductivity*, Cambridge University Press, 1933.

*Primary Examiner*—S. Clement Swisher
*Attorney, Agent, or Firm*—McGlew and Tuttle

[57] ABSTRACT

A current is applied to a thermistor or like heat sensitive element having a temperature-resistance characteristic to heat the heat sensitive element up to a temperature above the open air temperature and the heat sensitive element is held in the open air. Since the resistance value of the heat sensitive element varies with the amount of water vapor contained in the open air, the change in the resistance value is detected, from which the humidity of the open air is obtained. By temperature compensation, direct reading of absolute or relative humidity is made possible.

5 Claims, 14 Drawing Figures

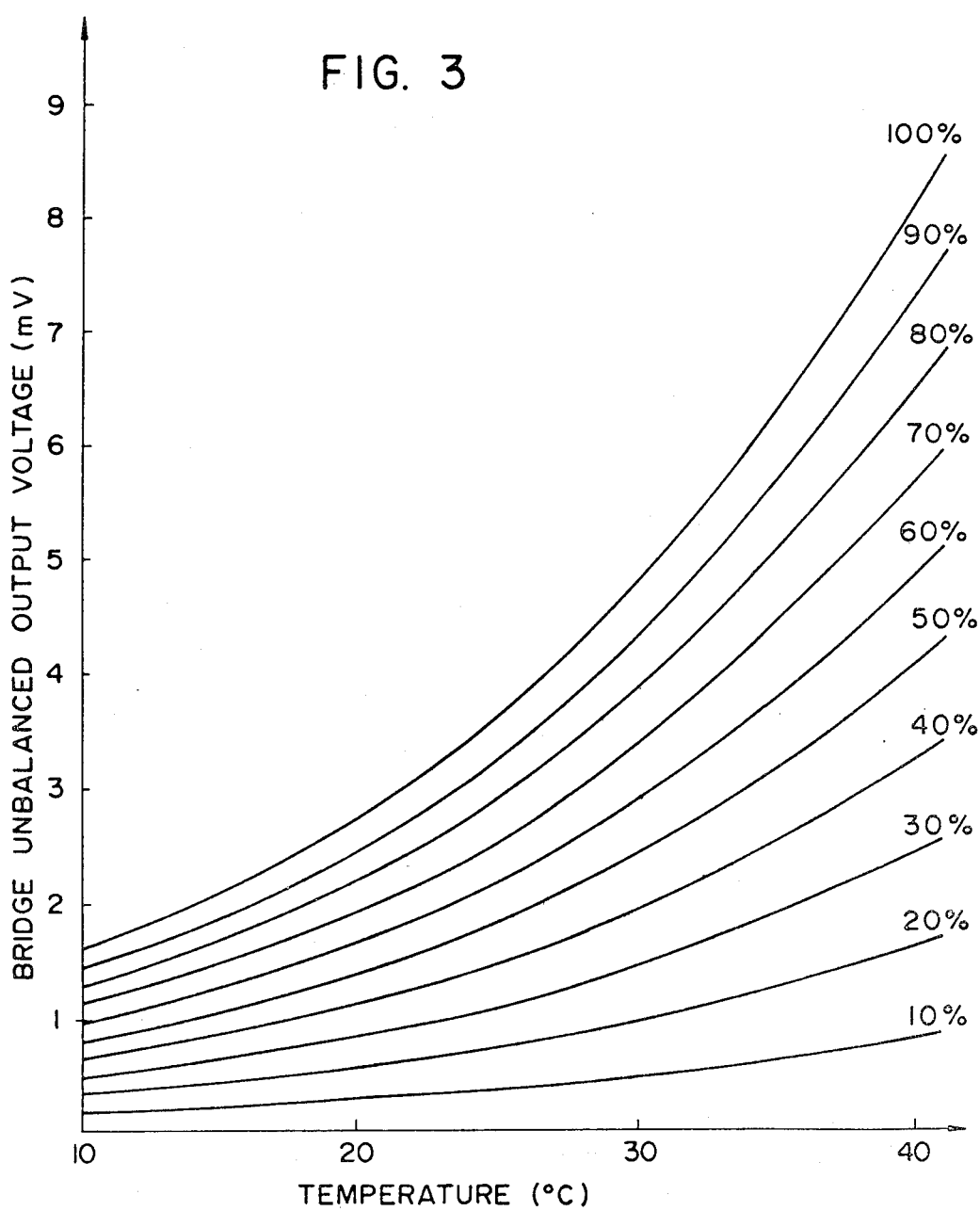

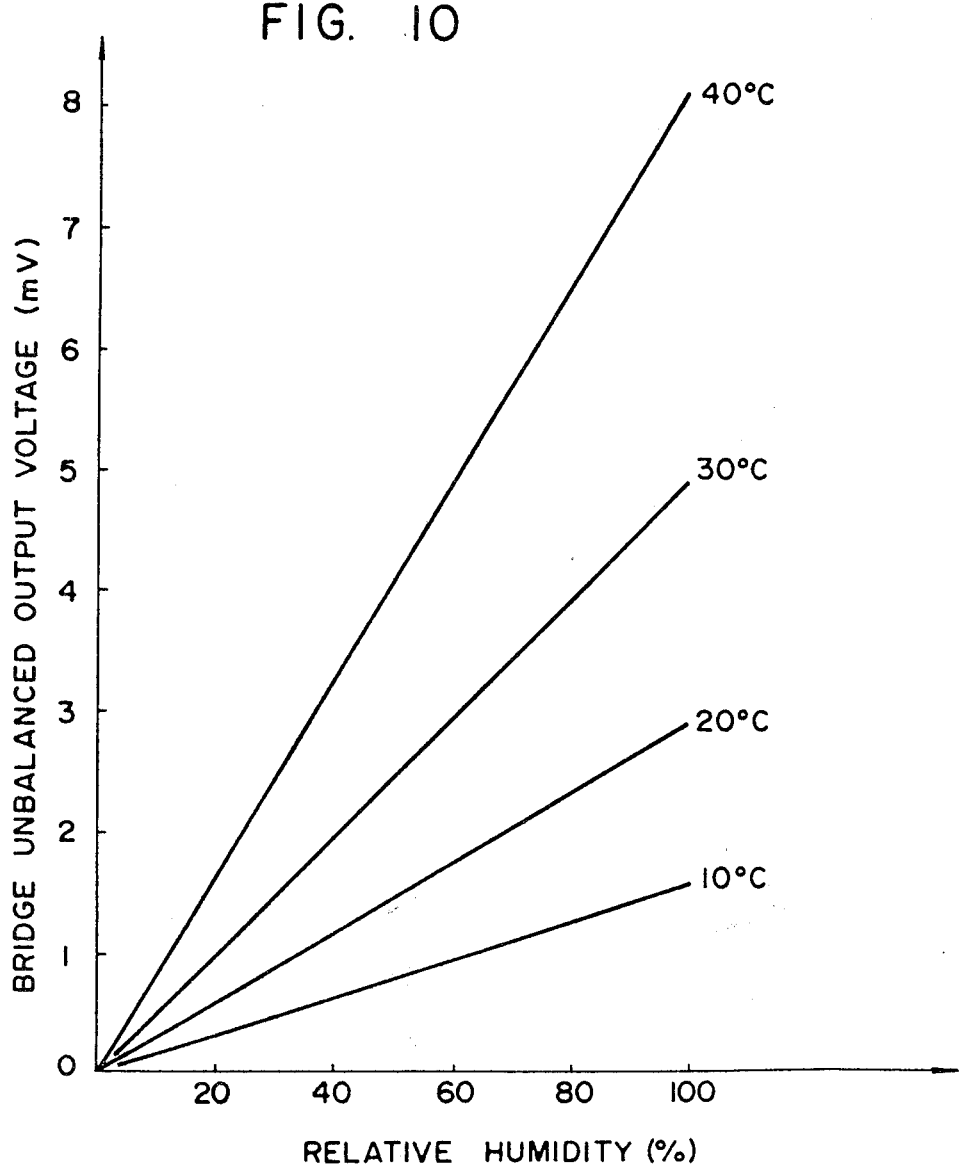

FIG. 12
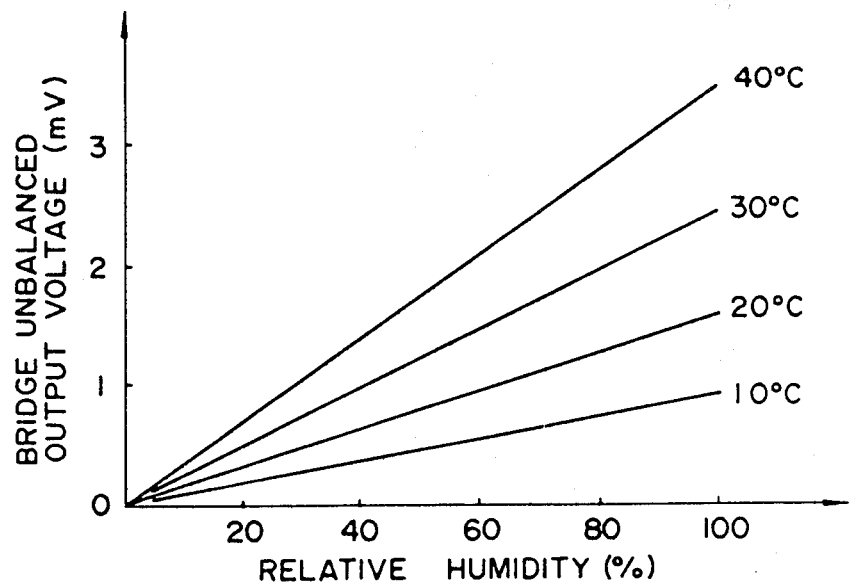
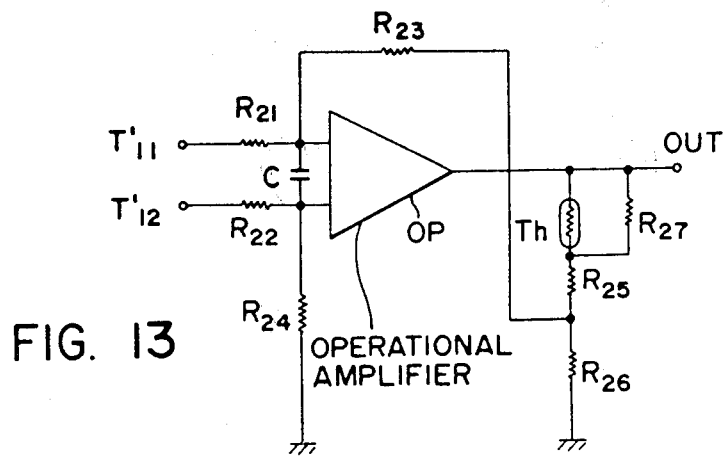
FIG. 13

HUMIDITY MEASURING METHOD

BACKGROUND OF THE INVENTION

1. Field of the Invention

This invention relates to a humidity measuring method and a hygrometer for electrically measuring humidity with high accuracy.

2. Description of the Prior Art

Heretofore, there have been employed a psychrometer, a hair hygrometer, a dew-point hygrometer, an absorption hygrometer and so forth for humidity measurement. The psychrometer is inexpensive and appreciably high in the accuracy of measurement, and hence is employed relatively widely; but this hygrometer requires constant wetting of a wet-bulb with water and therefore involves a water supply or replacement of a moisture absorbing gauze. The hair hygrometer is not satisfactory in the accuracy of measurement and the dew-point hygrometer involves cumbersome operations.

The absorption hygrometer is used for measurement of absolute humidity. In this case, a constant amount of air is passed through a U-shaped tube containing phosphorus pentoxide ($P_2O_5$) to entirely absorbe water vapor in the air by the phosphorus pentoxide and an increase in the mass of the phosphorus pentoxide is measured; since the increase in the mass corresponds to the water content in the air, the absolute humidity is obtained. But the absorption hygrometer is defective in that its measuring operation is complex.

SUMMARY OF THE INVENTION

It is an object of the present invention to electrically measure humidity easily with high accuracy.

Another object of the present invention is to permit direct reading of absolute humidity.

Yet another object of the present invention is to permit direct reading of relative humidity.

Briefly stated, according to the present invention, a current is applied to a heat sensitive element having a temperature-resistance characteristic to heat it above the open air temperature; the heat sensitive element is placed in the open air whose humidity is to be measured; a change in the resistance value of the heat sensitive element is detected which varies with the amount of water vapor contained in the open air; and the humidity of the air is measured from the change in the resistance value of the heat sensitive element. Further, the absolute or relative humidity of the air is directly read.

BRIEF DESCRIPTION OF THE DRAWINGS

FIG. 3 is a graph showing the relationship between temperature and a bridge unbalanced output voltage in the case of a thermistor being employed, with relative humidity used as a parameter;

FIG. 10 is a graph showing the relationship between relative humidity and a bridge unbalanced output voltage, with temperature used as a parameter;

FIG. 12 is a graph showing the relationship between relative humidity and a bridge unbalanced output voltage in the case of the platinum element being employed, with temperature used as a parameter; and FIGS. 13 and 14 are circuit diagrams respectively illustrating difference examples of temperature compensating amplifiers for use in this invention.

DESCRIPTION OF THE PREFERRED EMBODIMENTS

Figure 1:
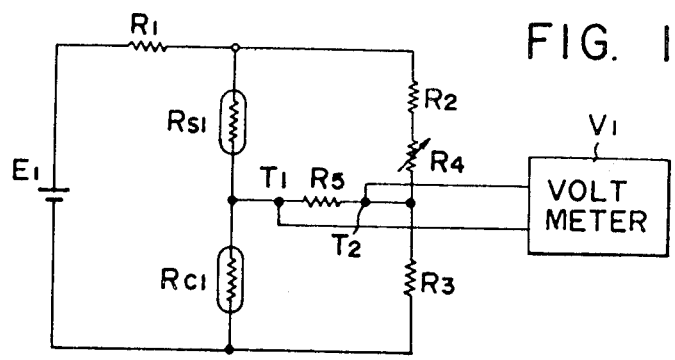
FIG. 1 is a circuit diagram illustrating an embodiment of this invention.

FIG. 1 is a circuit diagram illustrating an embodiment of its invention, which comprises a thermistor, platinum or like heat sensitive element $R_{S1}$ which is held to be exposable to the open air and has a temperature-resistance characteristic, a thermistor, platinum or like temperature compensating element $R_{C1}$ which is held in a completely dry state (in which the temperature compensating element is hermically sealed in an envelope together with a dry gas), a bridge circuit composed of two resistors $R_2$ and $R_3$ and a variable resistor $R_4$ for zero adjustment use, a power source $E_1$ connected with the bridge circuit via a resistor $R_1$ for current limiting use, a load resistor $R_5$ connected between terminals $T_1$ and $T_2$ and a voltmeter $V_1$ for measuring a bridge unbalanced output voltage which occurs across the load resistor $R_5$.

Figure 2:
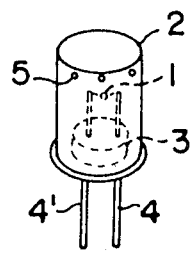
FIG. 2 is explanatory of a heat sensitive element structure of this invention.

The heat sensitive element $R_{S1}$ for use in the present invention has a construction such, for example, as shown in FIG. 2. In FIG. 2, reference numeral 1 indicates a thermistor coated with glass; 2 designates a metal case; 3 identifies a hermetic seal; 4 and 4' denote lead wires; and 5 represents holes. The metal case 2 is hermetically sealed by the hermetic seal 3 but has four to eight holes 5, for example, about 0.5 mm in diameter, permitting the thermistor 1 to be exposed to the open air. On the other hand, since the temperature compensating element $R_{C1}$ must be held in the absolutely dry state, it is sealed, together with a dry gas, in a metal case having no holes. In this case, however, the heat sensitive element $R_{S1}$ and the temperature compensating element $R_{C1}$ must be equipped with substantially the same current-voltage characteristic; furthermore, it is preferred that the both elements are placed adjacent to each other to hold them at the same temperature in an atmosphere with zero relative humidity.

For humidity measurement by the circuit depicted in FIG. 1, the first step is to apply a voltage via the resistor $R_1$ to the bridge circuit from the power source $E_1$ so that a predetermined current flows in the heat sensitive element $R_{S1}$ and the temperature compensating element $R_{C1}$ to put them in their self-heat state (about 200° C.). Then, for initial adjustment, the heat sensitive element $R_{S1}$ is held in an atmosphere with zero relative humidity and the variable resistance $R_4$ is adjusted so that a bridge unbalanced output voltage occuring across the load resistor $R_5$, i.e. between the terminals $T_1$ and $T_2$ may be reduced to zero. After the initial adjustment, the heat sensitive element $R_{S1}$ is contacted with the open air to start measurement. When the heat sensitive element $R_{S1}$ is exposed to the open air, if the amount of water vapor is large, that is, if the humidity of the open air is high, the amount of heat given off by the heat sensitive element $R_{S1}$ increases to decrease its temperature, resulting in its resistance value varying. The temperature drop of the heat sensitive element $R_{S1}$ is considered to be caused by a difference in thermal conductivity between the air and water vapor. The thermal conductivity K of a gas is given by the following equation (1):

$$K = \frac{1}{4}\left(\frac{9C_p}{C_v} - 5\right) \eta C_v \quad (1)$$

where $\eta$ is the coefficient of viscosity, Cv is the specific heat at constant volume and Cp is the specific heat at constant pressure.

In the present embodiment, the heat sensitive elements $R_{S1}$ and $R_{C1}$ are heated up to about 200° C. above the open air temperature for humidity measurement. The thermal conductivities of the air and water vapor at 200° C., obtained by the equation (1), are $8.64 \times 10^{-5}$ cal/cm.sec.°C. and $10.1 \times 10^{-5}$ cal/cm.sec.°C. respectively. Thus, at 200° C., the thermal conductivity of the water vapor is higher than the thermal conductivity of the air. Accordingly, an increase in the amount of water vapor contained in the air, that is, the humidity of air causes an increase in the thermal conductivity of that air around the heat sensitive element $R_{S1}$ which is the atmosphere whose humidity is to be measured, resulting in increased amount of heat given off by the heat sensitive element $R_{S1}$ to decrease its temperature.

A change in the resistance value of the heat sensitive element $R_{S1}$ by this temperature drop is very small, but the bridge circuit becomes unbalanced to yield a bridge unbalanced output voltage across the terminals $T_1$ and $T_2$. The unbalanced bridge output voltage corresponds to the change in the resistance value of the heat sensitive element $R_{S1}$ and increases with an increase in humidity. Also with an increase in the open air temperature, the bridge unbalanced output voltage increases.

FIG. 3 is a graph showing, with relative humidity used as a parameter, the relationships between the bridge unbalanced output voltage and the open air temperature in the case of using the thermistor of FIG. 2 as each of the heat sensitive element $R_{S1}$ and the temperature compensating element $R_{C1}$. As shown in FIG. 3, the bridge unbalanced output voltage varies not only with the humidity change but also with the open air temperature change, but if the bridge unbalanced output voltage and the open air temperature at the time of himidity measurement are both known, accurate humidity can be obtained using such a characteristic graph as depicted in FIG. 3. That is, by measuring the bridge unbalaned output voltage with the voltmeter $V_1$ and measuring the open air temperature at the time of humidity measurement, accurate humidity is available. Next, a description will be given of measured results of the relationship between the unbalanced bridge output voltage and the open air temperature in the present embodiment, using humidity as a parameter.

[1] In the case where there were employed in the circuit of FIG. 1, as the heat sensitive element $R_{S1}$ and the temperature compensating element $R_{C1}$, thermistors having such a current-voltage characteristic (at an ambient temperature of 25° C.) shown in Table 1:

TABLE 1

| Current (mA) | Voltage (V) | Temperature of the thermistor (°C.) |
|---|---|---|
| 0.1 | 0.828 | 25.6 |
| 0.2 | 1.59 | 26.6 |
| 0.5 | 2.96 | 34.8 |
| 1.0 | 3.62 | 49.5 |
| 2.0 | 3.58 | 72.5 |
| 5.0 | 2.84 | 117.0 |
| 10.0 | 2.21 | 162.0 |
| 15.0 | 1.87 | 182.5 |
| 20.0 | 1.65 | 217.5 |

Figure 4:
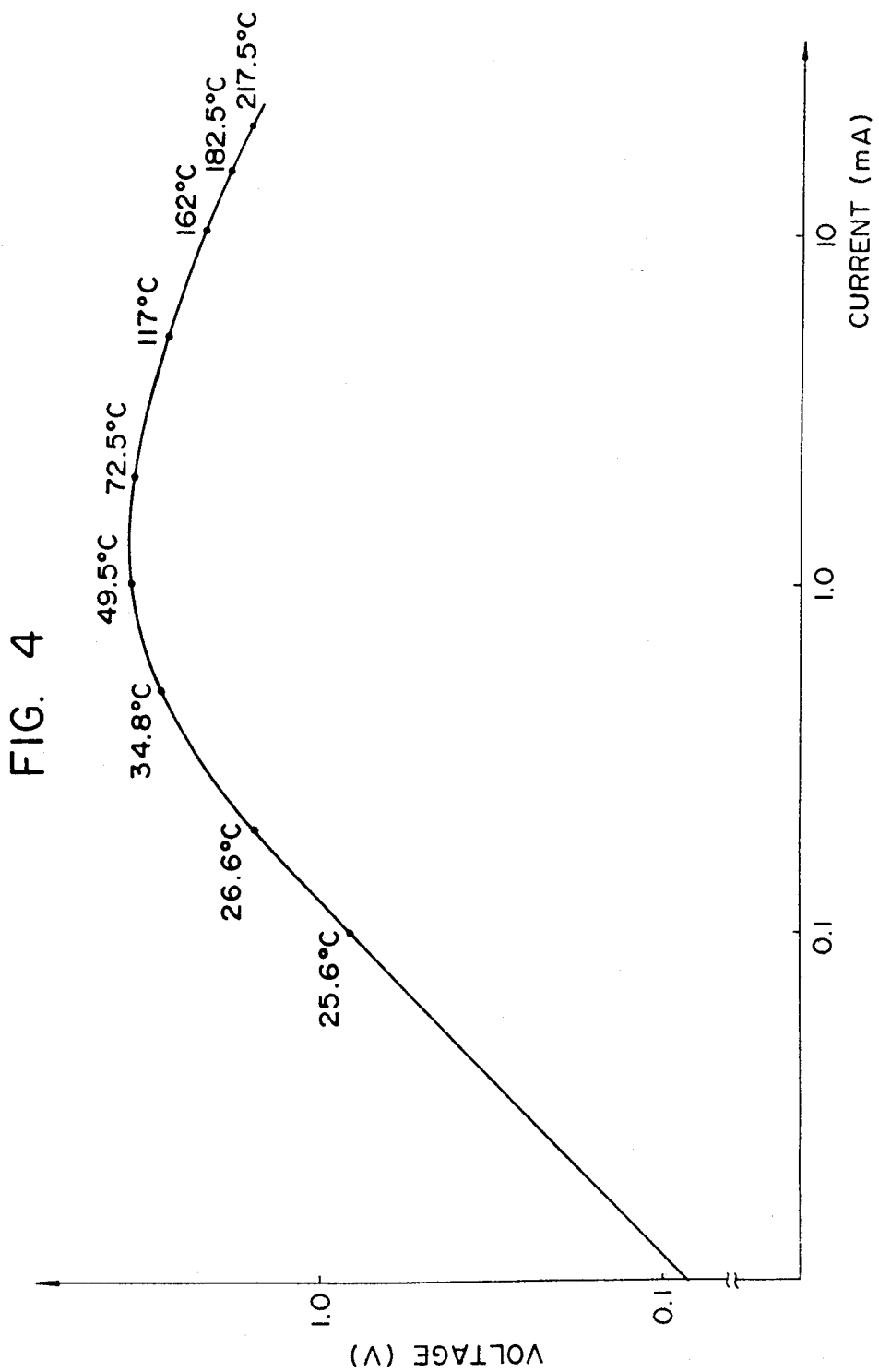
FIG. 4 is a graph showing an example of the current-voltage characteristic of the thermistor.

FIG. 4 shows a characteristic curve obtained by plotting the results given in Table 1. The resistance values of the resistors $R_1$ to $R_3$ and $R_5$ used were 0.389 KΩ, 10.04 KΩ, 10.04 KΩ and 49.47 KΩ respectively, and the voltage of the power source $E_1$ was 9.88 V. A current that flowed in the heat sensitive element $R_{S1}$ and the temperature compensating element $R_{C1}$ was 14.98 mA at an ambient temperature of 10° C., and the temperature of the heat sensitive element $R_{S1}$ and the temperature compensating element $R_{C1}$ was approximately 200° C.

It is FIG. 3 that is a graphical representation of the relationships between the bridge unbalanced output voltage across the result $R_5$ and the open air temperature which were measured using relative humidity as a parameter, with constants of the respective parts of measuring circuits set as described above and the heat sensitive element $R_{S1}$ and the temperature compensating element $R_{C1}$ put in their self-heat condition. Table 2 shows some of the measured data.

TABLE 2

| Temperature (C.°) | Relative humidity (%) | Output voltage (mA) |
|---|---|---|
| 10.0 | 80 | 1.26 |
|  | 60 | 0.94 |
|  | 40 | 0.63 |
|  | 20 | 0.31 |
| 20.0 | 80 | 2.32 |
|  | 60 | 1.74 |
|  | 40 | 1.16 |
|  | 20 | 0.58 |
| 30.0 | 80 | 3.90 |
|  | 60 | 2.29 |
|  | 40 | 1.95 |
|  | 20 | 0.97 |
| 40.0 | 80 | 6.50 |
|  | 60 | 4.88 |
|  | 40 | 3.25 |
|  | 20 | 1.63 |

As shown in FIG. 3, the bridge unbalanced output voltage varies with the humidity and temperature variations of the open air. Accordingly, by measuring the bridge unbalanced output voltage and the open air temperature at the time of humidity measurement, humidity can be obtained using such characteristic curves as shown in FIG. 3.

Figure 5:
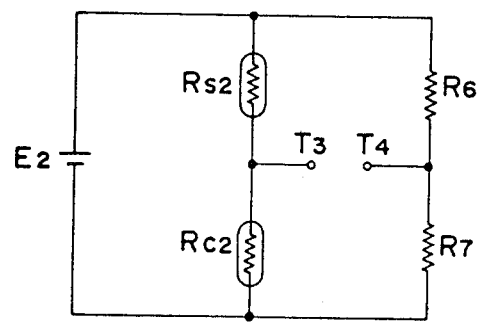
FIG. 5 is a circuit diagram for measuring the characteristic of the heat sensitive element for use in this invention.

[2] In the case where there were employed in a circuit of FIG. 5, as a heat sensitive element $R_{S2}$ and a temperature compensating element $R_{C2}$, platinum having such a current-voltage characteristic (at an ambient temperature of 250° C.) shown in Table 3:

TABLE 3

| Current (mA) | Voltage (mV) | Temperature of platinum (°C.) |
|---|---|---|
| 1.0315 | 2.9888 | 25.0 |
| 10.065 | 29.6052 | 29.223 |
| 20.01 | 59.6052 | 32.595 |
| 50.0 | 158.52 | 51.344 |
| 100.83 | 410.4 | 139.73 |
| 130.00 | 640.0 | 225.98 |
| 150.48 | 872.6 | 316.64 |
| 201.6 | 1680.2 | 596.47 |
| 300.0 | 3748.0 | 1129.5 |

Figure 6:
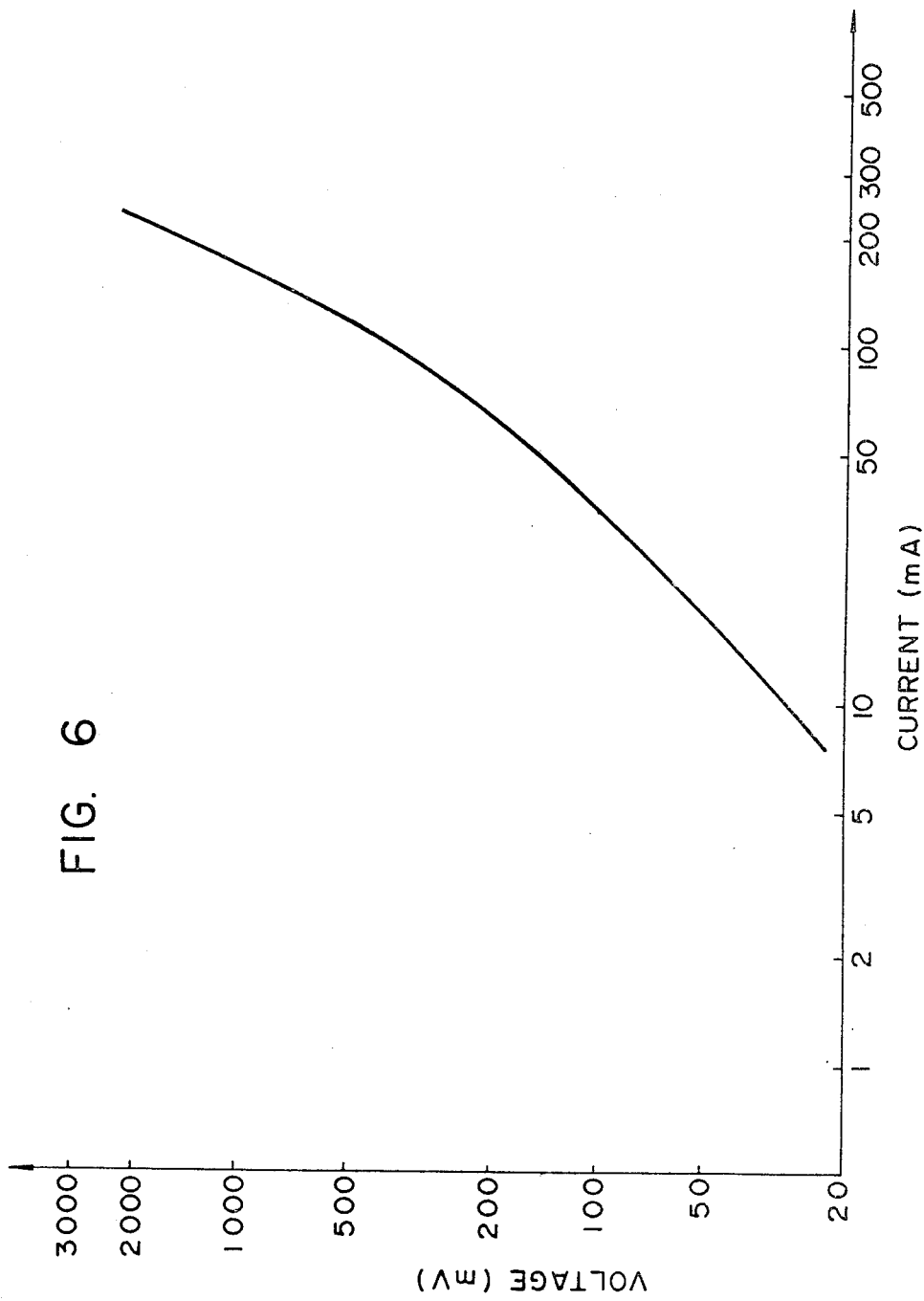
FIG. 6 is a graph showing an example of the current-voltage characteristic of platinum.

FIG. 6 shows a characteristic curve obtained by plotting the results given in Table 3. The resistance values of resistors $R_6$ and $R_7$ used were 1025.62 Ω and 922.2 Ω respectively, and a power source $E_2$ was adjusted so that the current flowing in the heat sensitive element $R_{S2}$ and the temperature compensating element $R_{C2}$ might be 130 mA.

Figure 7:
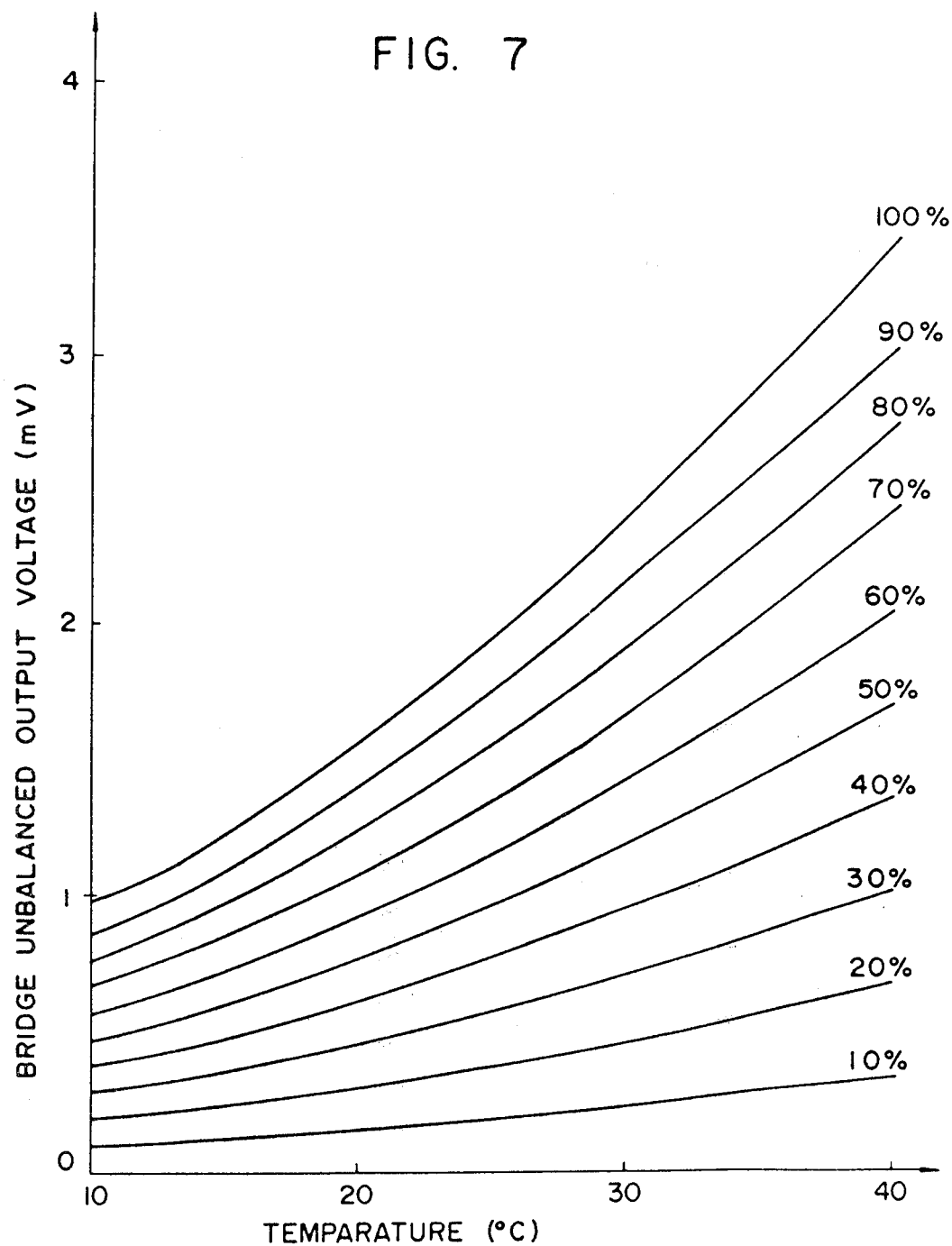
FIG. 7 is a graph showing the relationship between temperature and a bridge unbalanced output voltage in the case of a platinum element being employed, with relative humidity used as a parameter.

FIG. 7 is a graphical showing of the relationships between the bridge unbalanced output voltage across terminals $T_3$ and $T_4$ and the ambient temperature which were measured using relative humidity as a parameter, with the constants of the respective parts of the measuring circuit set and the heat sensitive element $R_{S2}$ and the temperature compensating element $R_{C2}$ put in their self-heat condition. Table 4 shows some of the measured data.

TABLE 4

| Temperature (°C.) | Relative humidity (%) | Output voltage (mA) |
|---|---|---|
| 10 | 80 | 0.752 |
|  | 60 | 0.564 |
|  | 40 | 0.376 |
|  | 20 | 0.188 |
| 20 | 80 | 1.256 |
|  | 60 | 0.942 |
|  | 40 | 0.628 |
|  | 20 | 0.314 |
| 30 | 80 | 1.936 |
|  | 60 | 1.452 |
|  | 40 | 0.968 |
|  | 20 | 0.484 |
| 40 | 80 | 2.76 |
|  | 60 | 2.07 |
|  | 40 | 1.384 |
|  | 20 | 0.69 |

As depicted in FIG. 7, the unbalanced bridge output voltage varies in response to the humidity and temperature variations of the open air. Accordingly, by measuring the bridge unbalanced output voltage and the open air temperature at the time of humidity measurement, humidity can be obtained utilizing the characteristic curves shown in FIG. 7 or the like.

Platinum reduces its resistance value with temperature drop, but the thermistor in the heated state increases its resistance value with temperature rise; accordingly, the bridge unbalanced output voltage in the case of employing platinum is reverse in polarity from the bridge unbalanced output voltage in the case of using the thermistor. As shown in FIGS. 3 and 7, however, the unbalanced output voltage exhibits the same tendency to variations with the humidity and ambient temperature changes irrespective of whether the platinum or the thermistor is used. Consequently, it is a matter of course that the heat sensitive temperature element and the temperature compensating element may be any of those which vary their resistance value with temperature.

Figure 8:
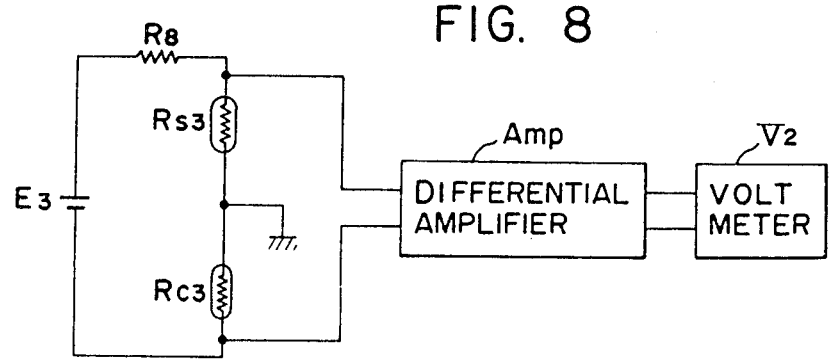
FIG. 8 is a circuit diagram illustrating another embodiment of this invention.

FIG. 8 is a circuit diagram illustrating another example of the circuit for the humidity measuring method of the present invention. Reference character $R_{S3}$ indicates a thermistor, platinum or like heat sensitive element which is held in a manner to be exposable to the open air; $R_{C3}$ designates a thermistor, platinum or like temperature compensating element which is held in the completely dry state; $R_8$ identifies a resistor for current limiting use; Amp denotes a differential amplifier for amplifying a difference between a voltage occurring across the heat sensitive element $R_{S3}$ and a voltage across the temperature compensating element; $V_2$ represents a voltmeter; and $E_3$ shows a power source. In this case, it is necessary that the heat sensitive element $R_{S3}$ and the temperature compensating element $R_{C3}$ have substantially the same current-voltage characteristic and are placed adjacent to each other.

The humidity measurement using the circuit of FIG. 8 starts with applying a voltage from the power source $E_3$ to the heat sensitive element $R_{S3}$ and the temperature compensating element $R_{C3}$ to put them in their self-heat state at a temperature (about 200° C.) above the open air temperature. After this, the heat sensitive element $R_{S3}$ is exposed to the open air to start the humidity measurement. Since the heat sensitive element $R_{S3}$ is held so that it may be exposed to the open air, the temperature of the heat sensitive element $R_{C3}$ lowers with an increase in the humidity of the open air and, at the same time, the resistance value of the heat sensitive element $R_{S3}$ also varies. On the other hand, since the temperature compensating element $R_{C3}$ is held in the completely dry state, its resistance value does not change with the variation in the humidity of the open air. Accordingly, a difference between the voltage across the heat sensitive element $R_{S3}$ and the voltage across the temperature compensating element $R_{C3}$ varies with the change in the humidity of the open air. In the present embodiment, this difference is amplified by the differential amplifier Amp and then measured by the voltmeter $V_2$.

The output voltage from the differential amplifier Amp increases with an increase in the humidity of the open air and, at the same time, varies with the temperature change of the open air; but, by measuring the output voltage from the differential amplifier Amp and the temperature of the open air at the time of humidity measurement, accurate humidity can be obtained using a conversion table or the like.

Figure 9:
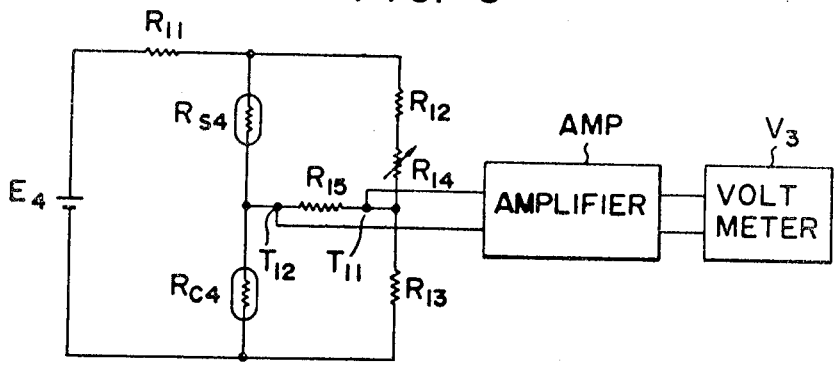
FIG. 9 is a circuit diagram illustrating another embodiment of this invention.

FIG. 9 is a circuit diagram illustrating another embodiment of the present invention, in which a bridge circuit is made up of a thermistor, platinum or like heat sensitive element $R_{S4}$ held in a manner to be freely exposable to the open air, a thermistor, platinum or like temperature compensating element $R_{C4}$ held in the completely dry state, resistors $R_{12}$ and $R_{13}$ and a variable resistor $R_{14}$ for zero adjustment use. A power source $E_4$ is connected via a resistor $R_{11}$ to the bridge circuit and a resistor $R_{15}$ is connected across terminals $T_{11}$ and $T_{12}$ of the bridge circuit. A voltage occurring across the terminals $T_{11}$ and $T_{12}$ is amplified by an amplifier AMP and its amplified output is applied to a voltmeter $V_3$. The bridge circuit is identical in construction with that employed in the foregoing embodiments.

In the case where thermistors are used as the heat sensitive element $R_{S4}$ and the temperature compensating element $R_{C4}$ and their voltage-current characteristics are such as shown in Table 1 and FIG. 4, the measured results shown in FIG. 3 and Table 2 are obtained as is the case with the foregoing embodiments. From the measured results, the bridge unbalanced output voltage and the relative humidity bear substantially linear relationships as shown in FIG. 10 in which temperature is used as a parameter.

The relationships between the relative himidity and the absolute temperature are such as given in Table 5, and the rate of increase (mV/g/m³) in the bridge unbalanced output voltage to the change in the absolute humidity at each temperature is such as shown in Table 6.

TABLE 5

| Temperature (°C.) | Relative humidity (%) | Absolute humidity (g/m³) | Output Voltage (mV) |
|---|---|---|---|
| 10 | 100 | 9.40 | 1.57 |
| | 80 | 7.52 | 1.26 |
| | 60 | 5.64 | 0.94 |
| | 40 | 3.76 | 0.63 |
| | 20 | 1.88 | 0.31 |
| 20 | 100 | 17.28 | 2.90 |
| | 80 | 13.824 | 2.32 |
| | 60 | 10.368 | 1.74 |
| | 40 | 6.912 | 1.16 |
| | 20 | 3.456 | 0.58 |
| 30 | 100 | 30.34 | 4.87 |
| | 80 | 24.272 | 3.90 |
| | 60 | 18.204 | 2.92 |
| | 40 | 12.136 | 1.95 |
| | 20 | 6.068 | 0.97 |
| 40 | 100 | 51.1 | 8.13 |
| | 80 | 40.88 | 6.50 |
| | 60 | 30.66 | 4.88 |
| | 40 | 20.44 | 3.25 |
| | 20 | 10.22 | 1.63 |

TABLE 6

| Temperature (°C.) | Rate of increase (mV/g/m³) |
|---|---|
| 10 | 0.167 |
| 20 | 0.1678 |
| 30 | 0.1605 |
| 40 | 0.1591 |

As seen from Table 6, the bridge unbalanced output voltage presents substantially the same rate of increase with respect to the increase in the absolute humidity at each temperature. Accordingly, by amplifying the bridge unbalanced output voltage across the terminals $T_{11}$ and $T_{12}$ of the bridge circuit by the amplifier AMP serving as a linear amplifier and applying the amplified output to the voltmeter $V_3$ graduated in terms of absolute humidity, the absolute humidity can be direct-read from the indication of the voltmeter $V_3$. In other words, an absolute hygrometer can be obtained which electrically measures absolute humidity.

The absolute humidity Dg/m³ is given by:

$$D = [804/(1+0.00366t)] \cdot (e/P_0) \quad (2)$$

where t is temperature (°C.), e is water vapor pressure (Pa) and $P_0$ is atmospheric pressure (Pa). The denominator 0.00366 shows the coefficient of thermal expansion of gas. As will be appreciated from the above expression, if the atmospheric temperature is changed while holding the water vapor content (or the water vapor pressure) in wet air constant, the value of D varies owing to an increase or decrease in the volume of the gas. Accordingly, using the following expression obtainable from the above expression:

$$e = [DP_0(1+0.00366t)]/804 \quad (3)$$

and assuming that the atmospheric pressure $P_0$ remains constant, the water vapor pressure e can be read from the output of the bridge per temperature compensating the value of D obtained. On the other hand, since the dew-point temperature of the atmosphere is dependent on the water vapor pressure e, the bridge output can be obtained, as a signal of the dew point, by applying it to the temperature compensating amplifier to eliminate the influence of expansion or contraction of the gas resulting from the temperature variation.

In the case of using platinum elements as the heat sensitive element $R_{S4}$ and the temperature compensating element $R_{C4}$, when the current-voltage characteristics of the platinum are such as shown in Table 3 and FIG. 6, the measured results shown in FIG. 7 and Table 4 are obtained as is the case with the fore going embodiment employing the platinum elements.

Figure 11:
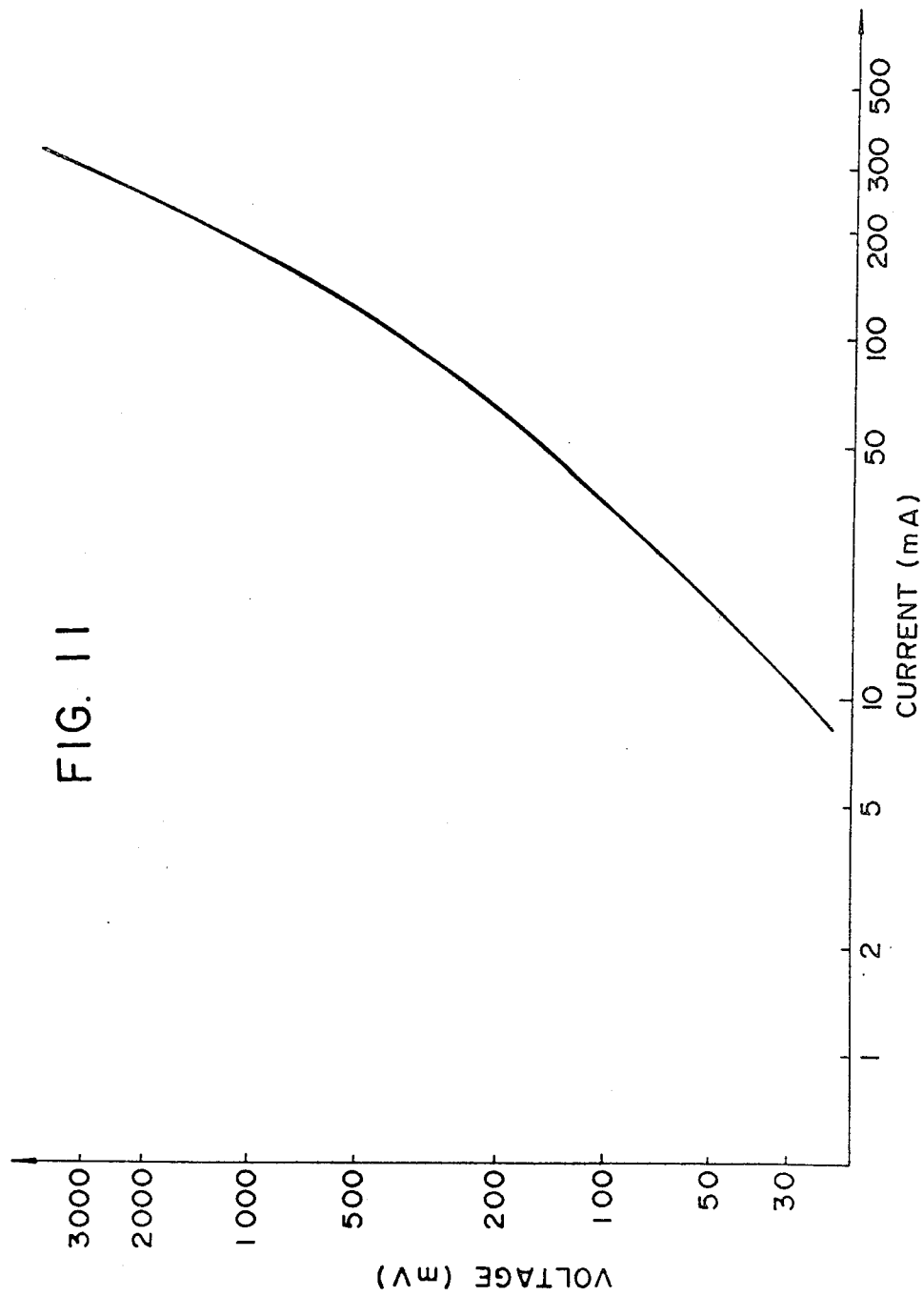
FIG. 11 is a graph showing another example of the current-voltage characteristic of the platinum element.

It is also possible to use platinum elements having such a current-voltage characteristic as shown in Table 7, and FIG. 11 shows a curve by plotting the values given in Table 7.

TABLE 7

| Current (mA) | Voltage (mV) | Temperature of platinum (°C.) |
|---|---|---|
| 1.0092 | 2.8348 | 25.0 |
| 10.019 | 28.3157 | 26.706 |
| 20.00 | 57.08 | 29.466 |
| 49.97 | 150.989 | 46.153 |
| 101.3 | 380.7 | 120.50 |
| 130.0 | 600.0 | 209.41 |
| 150.7 | 779.9 | 268.55 |
| 200.5 | 1462.3 | 504.01 |
| 300.1 | 3469.97 | 1049.8 |

From the measured results shown in Table 4, the relationships between the absolute humidity and the relative humidity shown in Table 8 are obtained. The relative humidity and the bridge unbalanced output voltage bear such relationships as shown in FIG. 12 in which temperature is used as a parameter.

TABLE 8

| Temperature (°C.) | Relative humidity (%) | Absolute humidity (g/m³) | Output voltage (mV) |
|---|---|---|---|
| 10 | 100 | 9.40 | 0.940 |
| | 80 | 7.52 | 0.752 |
| | 60 | 5.64 | 0.564 |
| | 40 | 3.76 | 0.376 |
| | 20 | 1.88 | 0.188 |
| 20 | 100 | 17.28 | 1.570 |
| | 80 | 13.324 | 1.256 |
| | 60 | 10.368 | 0.942 |
| | 40 | 6.912 | 0.628 |
| | 20 | 3.456 | 0.314 |
| 30 | 100 | 30.34 | 2.420 |
| | 80 | 24.272 | 1.936 |
| | 60 | 18.204 | 1.452 |
| | 40 | 12.136 | 0.968 |
| | 20 | 6.068 | 0.484 |
| 40 | 100 | 51.10 | 3.45 |
| | 80 | 40.88 | 2.76 |
| | 60 | 30.60 | 2.07 |
| | 40 | 20.44 | 1.38 |
| | 20 | 10.22 | 0.69 |

Table 9 shows how much the bridge unbalanced output voltage increases each time the absolute humidity increases by 1 g/m³ at each temperature.

TABLE 9

| Temperature (°C.) | Rate of increase (mV/g/m$^3$) |
|---|---|
| 10 | 0.1 |
| 20 | 0.0908 |
| 30 | 0.0798 |
| 40 | 0.068 |

In the case of employing platinum elements as the heat sensitive elements $R_{S4}$ and the temperature compensating elements $R_{C4}$, the rate of increase in the bridge unbalanced output voltage differs for each temperature, as shown in Table 9. However, since the bridge unbalanced output voltage varies in proportion to the change in the absolute humidity at one point of temperature, if the platinum elements are used in an atmosphere of constant ambient temperature, direct reading of the absolute humidity is possible by measuring the bridge unbalanced output voltage. For direct reading of the absolute humidity regardless of the ambient temperature, a temperature compensating amplifier whose amplification factor varies with temperature is connected across the terminals $T_{11}$ and $T_{12}$ and the rate of increase in the output voltage from the temperature compensating amplifier is held constant regardless of the ambient temperature. That is, the temperature compensating amplifier is used as the amplifier AMP.

FIG. 13 is a circuit diagram illustrating an example of the temperature compensating amplifier. In FIG. 13, reference characters $T_{11}'$ and $T_{12}'$ indicate terminals for connection with the terminals $T_{11}$ and $T_{12}$ of the bridge circuit; OP designates an operational amplifier; Th identifies a thermistor; $R_{21}$ to $R_{27}$ denote resistors; C represents a capacitor; and OUT shows an output terminal. In this case, since the thermistor Th is connected to a feedback circuit of the operational amplifier OP, the amplification factor of the operational amplifier OP varies with the ambient temperature. As a consequence, the rate of increase in the output voltage available from the output terminal OUT can be made constant regardless of the ambient temperature. Accordingly, by connecting a voltmeter to the output terminal OUT, direct reading of absolute humidity is possible.

It is a matter of course that the temperature compensating amplifier may be any type of amplifier so long as the abovesaid object can be achieved. Also in the case of using thermistors as the heat sensitive element and the temperature compensating element, the accuracy of measurement can be enhanced by employing such a temperature compensating amplifier.

Since relative humidity varies with the open air temperature as described previously, a relative hygrometer can be constituted by such an arrangement that changes the amplification factor of the amplifier AMP in FIG. 9 with temperature and permits direct reading of the relative humidity by the voltmeter $V_3$ graduated in terms of relative humidity.

Figure 14:
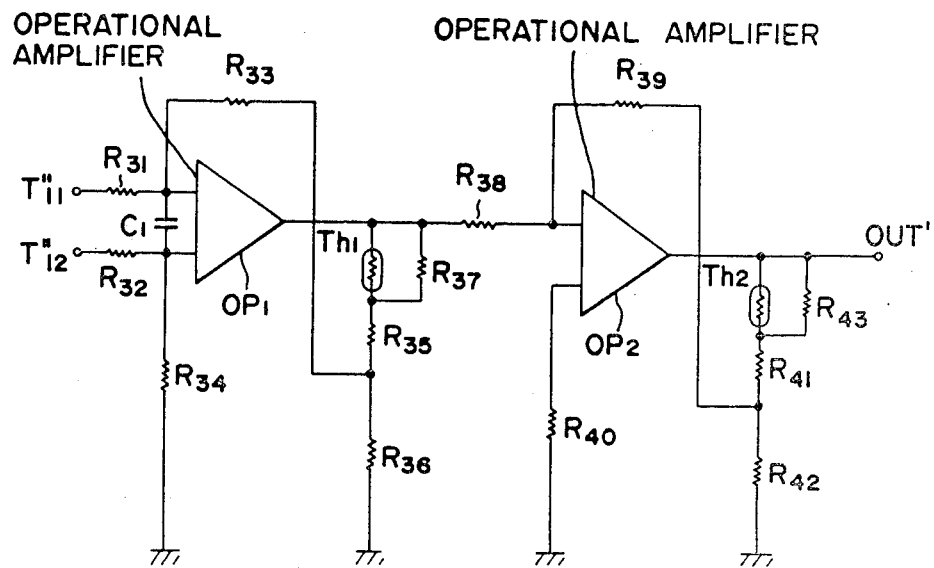

FIG. 14 is a circuit diagram illustrating an example of a temperature compensating amplifier whose amplification factor is changed with temperature for direct reading of the relative humidity. In FIG. 14, reference characters $T_{11}''$ and $T_{12}''$ indicate terminals for connection with the terminals $T_{11}$ and $T_{12}$ of the bridge circuit in FIG. 9; $R_{31}$ to $R_{43}$ designate resistors; $C_1$ identifies a capacitor; $OP_1$ and $OP_2$ denote operational amplifiers; $Th_1$ and $Th_2$ represent thermistors; and OUT' shows an output terminal for connection with the voltmeter $V_3$.

The operational amplifier $OP_1$ amplifies the bridge unbalanced output voltage and provides the amplified output to the operational amplifier $OP_2$ of the next stage. Since the thermistor $Th_1$ is connected to a feedback circuit of the operational amplifier $OP_1$, the resistance value of the thermistor varies with the open air temperature to cause a change in the amplification factor of the operational amplifier $OP_1$. The operational amplifier $OP_2$ is identical in construction with the operational amplifier $OP_1$, and accordingly the amplification factor of the operational amplifier $OP_2$ varies with the open air temperature.

When temperature falls, the resistance values of the thermistors $Th_1$ and $Th_2$ increase to cause a decrease in the feedback from the output side to the input side of the operational amplifiers $OP_1$ and $OP_2$, resulting in their amplification factor becoming large. Accordingly, by determining the change in the amplification factor with temperature in a manner to compensate for the variations in temperature and relative humidity shown in FIG. 3, relative humidity can be read directly from the voltmeter $V_3$ connected to the output terminal OUT'. The bridge unbalanced output voltage, for example, at 30° C., is 2.5 mV to indicate a relative humidity of 50%; in the case where the amplification factor at this time is regarded as 100 and a voltage of 250 mV is yielded, if the temperature drops to 20° C., the bridge unbalanced output voltage becomes 1.4 mV. Then, by changing the amplification factor to 178 corresponding to the temperature change as described above, the voltage of 250 mV is provided again, and accordingly the indication of the voltmeter $V_3$ shows the relative humidity 50% without undergoing any change. Therefore, even if the open air temperature changes without any change in the relative humidity, the output voltage at the output terminal OUT' does not vary; hence, the relative humidity can be indicated on the voltmeter $V_3$ so that it can be read directly therefrom. Since the temperature compensating amplifier of FIG. 14 is easy of increasing its amplification factor with temperature change, as compared with the temperature compensating amplifier of FIG. 13, the former is suitable for use in measuring the relative humidity regardless of temperature.

As has been described in the foregoing, according to the present invention, a current is applied to a thermistor, platinum or like heat sensitive element to heat it up to a temperature above the open air temperature; the heat sensitive element is held in the open air to cause its resistance value to vary with the quantity of water vapor contained in the open air; and the resistance value is measured, thereby to obtain relative or absolute humidity. The absolute humidity indicates the quantity of water vapor (g/m$^3$) contained in the open air and when the open air temperature drops to the temperature at which this quantity of water vapor corresponds to the quantity of saturated water vapor, the temperature at that time represents the dew-point temperature.

Accordingly, the dew-point temperature can be read directly by amplifying a signal of the absolute humidity with the temperature compensating amplifier to eliminate the influence of expansion or contraction of the gas due to temperature variations. In other words, by applying the output of the humidity sensor to such a temperature compensating amplifier, it is possible to obtain a dew point meter which is directly graduated in dew point for giving a reading of dew-point temperature.

The voltmeter may also be a digital voltmeter; in this case, by providing the amplifier for amplifying the bridge unbalanced output voltage with the temperature compensating characteristic corresponding to the purpose of measuring the absolute or relative humidity and the characteristic of the heat sensitive element used, the absolute or relative humidity can be read directly from the digital voltmeter without regard to variations in the open air temperature. This leads to the advantage of easy and highly accurate humidity measurement.

It will be apparent that many modifications and variations may be effected without departing from the scope of the novel concepts of this invention.

What is claimed is:

1. A hygrometer comprising:
a heat sensitive element having a temperature-resistance characteristic and held in a manner to be exposable to the open air;
a temperature compensating element having substantially the same temperature-resistance characteristic as the heat sensitive element and held in a completely dry state;
two resistors;
the heat sensitive element, the temperature compensating element and two resistors forming a bridge circuit;
a power source for supplying a current to the heat sensitive element and the temperature compensating element to heat them up to a temperature above the open air temperature; and
a temperature compensating amplifier for amplifying an unbalanced output voltage from the bridge circuit, caused by a change in the resistance value of the heat sensitive element corresponding to the amount of water vapor contained in the open air, in such a manner that the amplification factor may vary with the open air temperature and the output corresponding to the relative humidity of the open air may have nothing to do with the open air temperature; and
voltage measuring means supplied with the output voltage from the temperature compensating amplifier to indicate the relative humidity.

2. A hygrometer according to claim 1, wherein the heat sensitive element and the temperature compensating elements are formed by thermistors.

3. A hygrometer according to claim 1, wherein the heat sensitive element and the temperature compensating element are formed by platinum elements.

4. A hygrometer according to claim 1, wherein the temperature compensating amplifier is formed by connecting to a feedback circuit of an operational amplifier a thermistor whose resistance value varies with the open air temperature.

5. A hygrometer comprising:
a heat sensitive element having a temperature-resistance characteristic and held in a manner to be exposable to the open air;
a temperature compensating element having substantially the same temperature-resistance characteristic as the heat sensitive element and held in a completely dry state;
two resistors;
the heat sensitive element, the temperature compensating element and two resistors forming a bridge circuit;
a power source for supplying a current to the heat sensitive element and the temperature compensating element to heat them up to a temperature above the open air temperature;
voltage measuring means for measuring as the absolute humidity of the open air, an unbalanced output voltage from the bridge circuit which is caused by a change in the resistance value of the heat sensitive element which varies with the amount of water vapor contained in the open air;
the heat sensitive element and the temperature compensating element comprising thermistors;
the heat sensitive element and the temperature compensating element comprising thermistors;
the heat-sensitive and temperature compensating elements being connected in series, said power source connected to the heat-sensitive element and temperature compensating element in series and said voltage measuring means being connected between a series connection of the heat-sensitive and temperature-compensating element and a connection between said two resistors;
said power source being operable to supply a current to the heat-sensitive and temperature-compensating elements sufficient to raise their temperature to about 200°.

* * * * *